(12) United States Patent
Bourque

(10) Patent No.: US 8,679,177 B2
(45) Date of Patent: Mar. 25, 2014

(54) METHOD OF IMPLANTING A BLOOD PUMP SYSTEM

(75) Inventor: Kevin Bourque, Reading, MA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/414,041

(22) Filed: Mar. 7, 2012

(65) Prior Publication Data

US 2012/0165931 A1 Jun. 28, 2012

Related U.S. Application Data

(62) Division of application No. 12/650,017, filed on Dec. 30, 2009, now Pat. No. 8,152,845.

(51) Int. Cl.
*A61M 1/10* (2006.01)

(52) U.S. Cl.
USPC .......................................................... 623/3.1

(58) Field of Classification Search
USPC .......................................................... 623/3.1
See application file for complete search history.

(56) References Cited

U.S. PATENT DOCUMENTS

| | | | |
|---|---|---|---|
| 4,458,366 A | 7/1984 | MacGregor |
| 4,688,998 A | 8/1987 | Olsen et al. |
| 4,769,031 A | 9/1988 | McGough et al. |
| 5,055,005 A | 10/1991 | Kletschka |
| 5,098,369 A | 3/1992 | Heilman et al. |
| 5,139,517 A | 8/1992 | Corral |
| 5,195,877 A | 3/1993 | Kletschka |
| 5,222,980 A | 6/1993 | Gealow |
| 5,275,580 A | 1/1994 | Yamazaki |
| 5,456,714 A | 10/1995 | Owen |
| 5,470,208 A | 11/1995 | Kletschka |
| 5,708,346 A | 1/1998 | Schob |
| 5,814,005 A | 9/1998 | Barra et al. |
| 5,827,316 A | 10/1998 | Young et al. |
| 5,843,088 A | 12/1998 | Barra et al. |
| 5,984,956 A | 11/1999 | Tweden et al. |
| 6,001,056 A | 12/1999 | Jassawalla et al. |

(Continued)

FOREIGN PATENT DOCUMENTS

| CA | 2526920 | 2/2009 |
|---|---|---|
| CN | 1842354 | 10/2006 |

(Continued)

OTHER PUBLICATIONS

U.S. Appl. No. 12/472,812, Thomas et al.

(Continued)

*Primary Examiner* — Thomas J Sweet
*Assistant Examiner* — Matthew Schall
(74) *Attorney, Agent, or Firm* — Kilpatrick Townsend and Stockton LLP

(57) ABSTRACT

A method of implanting a blood pump system in a patient requiring treatment includes creating an opening in an epicardium of a heart to access an interior chamber of the heart and implanting a blood pump such that an inlet port of a pump housing is in fluid communication with the interior chamber of the heart through the opening. The pump housing has a first external surface adjacent to the inlet port such that it is substantially adjacent to the epicardium of the heart when implanted. In some embodiments, a first external surface contacts the epicardium when implanted. The blood pump is then secured to the exterior wall of the heart. In some embodiments, the blood pump is secured using a mounting cuff.

24 Claims, 6 Drawing Sheets

(56) References Cited

U.S. PATENT DOCUMENTS

| | | | |
|---|---|---|---|
| 6,050,975 A | 4/2000 | Poirer |
| 6,066,085 A | 5/2000 | Heilman et al. |
| 6,146,325 A | 11/2000 | Lewis et al. |
| 6,254,564 B1 | 7/2001 | Wilk et al. |
| 6,346,071 B1 | 2/2002 | Mussivand |
| 6,390,976 B1 | 5/2002 | Spence et al. |
| 6,669,708 B1 | 12/2003 | Nissenbaum et al. |
| 6,673,043 B1 | 1/2004 | Landesberg |
| 6,689,147 B1 | 2/2004 | Koster |
| 6,705,988 B2 | 3/2004 | Spence et al. |
| 6,726,648 B2 | 4/2004 | Kaplon et al. |
| 6,732,501 B2 | 5/2004 | Yu et al. |
| 6,802,806 B2 | 10/2004 | McCarthy et al. |
| 6,808,498 B2 | 10/2004 | Laroya et al. |
| 6,863,677 B2 | 3/2005 | Breznock |
| 6,942,672 B2 | 9/2005 | Heilman et al. |
| 6,994,666 B2 | 2/2006 | Shannon et al. |
| 7,018,384 B2 | 3/2006 | Skakoon |
| 7,048,681 B2 | 5/2006 | Tsubouchi et al. |
| 7,056,286 B2 | 6/2006 | Ravenscroft et al. |
| 7,077,801 B2 | 7/2006 | Haverich |
| 7,214,234 B2 | 5/2007 | Rapacki et al. |
| 7,404,792 B2 | 7/2008 | Spence et al. |
| 7,462,019 B1 | 12/2008 | Allarie et al. |
| 8,152,845 B2 | 4/2012 | Bourque |
| 2002/0045846 A1 | 4/2002 | Kaplon et al. |
| 2002/0095210 A1 | 7/2002 | Finnegan et al. |
| 2003/0023255 A1 | 1/2003 | Miles et al. |
| 2003/0040765 A1 | 2/2003 | Breznock |
| 2003/0130668 A1 | 7/2003 | Nieman et al. |
| 2004/0002624 A1 | 1/2004 | Yu et al. |
| 2004/0153112 A1 | 8/2004 | Nissenbaum et al. |
| 2004/0171905 A1 | 9/2004 | Yu et al. |
| 2004/0236170 A1 | 11/2004 | Kim |
| 2005/0033107 A1 | 2/2005 | Tsubouchi |
| 2005/0101982 A1 | 5/2005 | Ravenscroft et al. |
| 2005/0131451 A1 | 6/2005 | Kleshinski et al. |
| 2005/0149093 A1 | 7/2005 | Pokorney |
| 2005/0154411 A1 | 7/2005 | Breznock et al. |
| 2005/0209502 A1 | 9/2005 | Schmid et al. |
| 2005/0251187 A1 | 11/2005 | Beane et al. |
| 2006/0036313 A1 | 2/2006 | Vassiliades |
| 2006/0089707 A1 | 4/2006 | Vassiliades et al. |
| 2006/0099716 A1 | 5/2006 | Tipler et al. |
| 2006/0142634 A1 | 6/2006 | Anstadt et al. |
| 2006/0161193 A1 | 7/2006 | Beane et al. |
| 2007/0088375 A1 | 4/2007 | Beane et al. |
| 2007/0100363 A1 | 5/2007 | Dollar et al. |
| 2007/0106315 A1 | 5/2007 | Gregoric et al. |
| 2007/0134993 A1 | 6/2007 | Tamez et al. |
| 2007/0167968 A1 | 7/2007 | Pandey |
| 2007/0167969 A1 | 7/2007 | Pandey |
| 2007/0173879 A1 | 7/2007 | Pandey |
| 2007/0265643 A1 | 11/2007 | Beane et al. |
| 2008/0009668 A1 | 1/2008 | Cohn |
| 2008/0009887 A1 | 1/2008 | Cohn |
| 2008/0009891 A1 | 1/2008 | Cohn |
| 2008/0076959 A1 | 3/2008 | Farnan et al. |
| 2009/0012552 A1 | 1/2009 | Pandey et al. |
| 2009/0171136 A1 | 7/2009 | Shambaugh |
| 2011/0118833 A1 | 5/2011 | Reichenbach et al. |
| 2011/0160850 A1 | 6/2011 | Bourque |
| 2012/0059212 A1 | 3/2012 | LaRose et al. |
| 2012/0226096 A1 | 9/2012 | Callaway et al. |

FOREIGN PATENT DOCUMENTS

| | | |
|---|---|---|
| DE | 10108809 A1 | 9/2002 |
| EP | 1706168 | 10/2006 |
| JP | 2007510522 | 4/2007 |
| WO | WO 00/74747 | 12/2000 |
| WO | WO03001980 A2 | 1/2003 |
| WO | WO2004014456 A2 | 2/2004 |
| WO | WO 2005/046783 | 5/2005 |
| WO | WO2007038109 A2 | 4/2007 |
| WO | WO 2008/131453 | 10/2008 |
| WO | WO2009085243 A1 | 7/2009 |

OTHER PUBLICATIONS

Authorized Officer K. Bichlmayer, International Search Report and Written Opinion of the International Searching Authority, PCT/US2009/069836, mailed Sep. 20, 2010.

Barletta et al., "Design of a Bearingless Blood Pump," in Proceedings Third International Symposium on Magnetic Suspension Technology, Tallahassee, FL, 1995, pp. 265-274.

Non-Final Office Action for U.S. Appl. No. 12/650,017 dated Jun. 27, 2011, 10 pages.

Notice of Allowance for U.S. Appl. No. 12/650,017 dated Jan. 4, 2012, 11 pages.

Authorized Officer Philp Jones, International Search Report and Written Opinion of the International Searching Authority for Application No. PCT/US2012/027481 dated Jun. 6, 2012, 16 pages.

Authorized Officer Athina Nickitas-Etienne, PCT Notification Concerning Transmittal of International Preliminary Report on Patentability, PCT/US2009/069836, mailed Jul. 12, 2012, 9 pages.

International Preliminary Report on Patentability for PCT/US2012/027481, issued Sep. 3, 2013, 10 pages.

METHOD OF IMPLANTING A BLOOD PUMP SYSTEM

CROSS-REFERENCE TO RELATED APPLICATIONS

This application is a divisional of and claims the benefit under 35 U.S.C. §121 of U.S. application Ser. No. 12/650,017, filed Dec. 30, 2009, the entire contents of which is incorporated herein by reference.

TECHNICAL FIELD

This document relates to implanted medical pump systems, such as ventricular assist blood pumps, and related components, such as mounting cuffs used to attach the assist pumps to the epicardium of a heart. This document also describes a method of implanting such a medical pump system.

BACKGROUND

The human heart is a complex and critical pump. Due to various pathologies, the heart can become dysfunctional, acutely or chronically. When damage to the heart has become sufficiently symptomatic by clinical measures, the heart may be diagnosed as cardiomyopathic, a form of heart failure. In such a situation, a doctor can recommend mechanical assistance among the few therapeutic options that include pharmacologic therapy and heart transplantation. Where an afflicted person is scheduled to receive a transplant, mechanical assistance may be a choice of therapy until a donor heart becomes available.

Blood pumps are commonly used to provide mechanical augmentation to the pumping performed by the left and/or right ventricles of the heart. Ventricular assistance may be provided by an implantable pump that is connected in parallel with the person's heart and may be implanted adjacent to the heart, in contact with the heart, or in a remote location such as the abdomen. The choice of blood pump and implantation location can be determined by factors such as the size of the pump, the style of pump, the duration of mechanical assistance as required by the patient's condition, the size of the patient, and the like.

SUMMARY

An implantable blood pump system is described that includes a blood pump housing and a mounting cuff. The blood pump housing at least partially contains a pump drive system adapted to transfer blood from an interior chamber of a heart and return the blood to a circulatory system. The blood pump housing includes an inlet port adapted to provide a passage for the flow of blood from the interior chamber of the heart into an interior space of the pump housing and an outlet port adapted to provide a passage for the flow of blood from an interior space of the pump housing to the circulatory system. The blood pump housing includes a first external surface adjacent to the inlet port and a second external surface adjacent to the first external surface. The first external surface is adapted to be implanted substantially adjacent to an outer surface of an epicardium of the heart. The second external surface at least partially defines an outside perimeter of the pump housing. The mounting cuff is adapted to mechanically couple to the second external surface and to the epicardium of the heart. The mounting cuff can allow for the placement of the pump against the epicardium without a gap, thus minimizing the effective size of the pump. The mounting cuff can also provide a mechanical advantage to the attachment and consequently greater resistance to myocardial trauma.

The second external surface and the first external surface can be part of a continuous surface, but on different planes. The second external surface of the pump housing can be substantially perpendicular to the first external surface and can have a larger outside perimeter than the inlet port. For example, the second external surface can be substantially cylindrical and the first external surface can be substantially toroidal. The inlet port can at least partially define an opening in the first external surface. In some embodiments, the inlet port can include an inlet cannula that extends from the first external surface. The inlet cannula can extend at least partially into the epicardium. In some embodiments, the inlet cannula can be elongate and adapted to traverse the epicardium and fluidly connect the interior chamber of the heart with the interior space of the pump housing. An inlet cannula can be reversibly coupled to the pump housing. An inlet cannula can be substantially cylindrical. In some embodiments, the outlet port can at least partially define an opening in the second external surface.

The mounting cuff can substantially encircle the second surface. The mounting cuff can be adapted to be coupled to the exterior wall of the heart using sutures.

In some embodiments, the system can further include a removable plug adapted to fit within an elongate inlet cannula to substantially block the flow of fluid through the interior channel.

According to another aspect, a method of implanting a blood pump system is described. The method includes creating an opening in an epicardium of a heart to access an interior chamber of the heart, implanting a blood pump, fluidly connecting an outlet port of the blood pump to the circulatory system, and securing a mounting cuff to the exterior wall of the heart. The blood pump is implanted such that an inlet port of a pump housing is in fluid communication with the interior chamber of the heart and a first external surface adjacent to the inlet port is substantially adjacent to the epicardium of the heart. The blood pump is adapted to transfer blood from the inlet port to the outlet port. The mounting cuff is adapted to be coupled to a second external surface of the pump housing. The second external surface is located adjacent to the first external surface and at least partially defines an outside perimeter of the pump housing. In some embodiments, the method can additionally include securing the mounting cuff to the second external surface of the pump housing. The step of securing the mounting cuff to the second external surface of the pump housing can be performed prior to the step of securing the mounting cuff to the epicardium of the heart. The step of securing the mounting cuff to the epicardium of the heart can, in other embodiments, be performed prior to the step of securing the mounting cuff to the second external surface of the pump housing.

The method can further include implanting an inlet cannula. The inlet cannula can be adapted to traverse the wall of the heart. The inlet cannula includes an interior channel that fluidly connects the interior chamber of the heart with the inlet port of the pump housing. The method can further include a step of coupling the pump housing to the inlet cannula.

The mounting cuff can, in some embodiments, be secured to the exterior wall of the heart while the first surface of the pump housing is positioned substantially adjacent to the epicardium of the heart.

The step of implanting can, in some embodiments, include causing the inlet port to contact the epicardium of the heart.

According to another aspect, a mounting cuff is described. The mounting cuff is adapted to mechanically couple a blood pump to an epicardium of a heart to a blood pump. The mounting cuff can include an inner surface adapted to fit around an outer perimeter of a blood pump.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

An implanted blood pump system can include a blood pump housing and a mounting cuff that can be used to secure the blood pump housing to the epicardium of a heart. The mounting cuff may be preferentially located around the outside perimeter of the blood pump housing as an advantageous alternative to the typical location around the pump's inlet port cannula. The blood pump housing at least partially contains a pump drive system adapted to transfer blood from an interior chamber of a heart and return the blood to a circulatory system. The mounting cuff, which may be sewn onto the heart, can securely hold the blood pump in contact with the wall of the heart while simplifying the implantation of the blood pump.

Figure 1A:
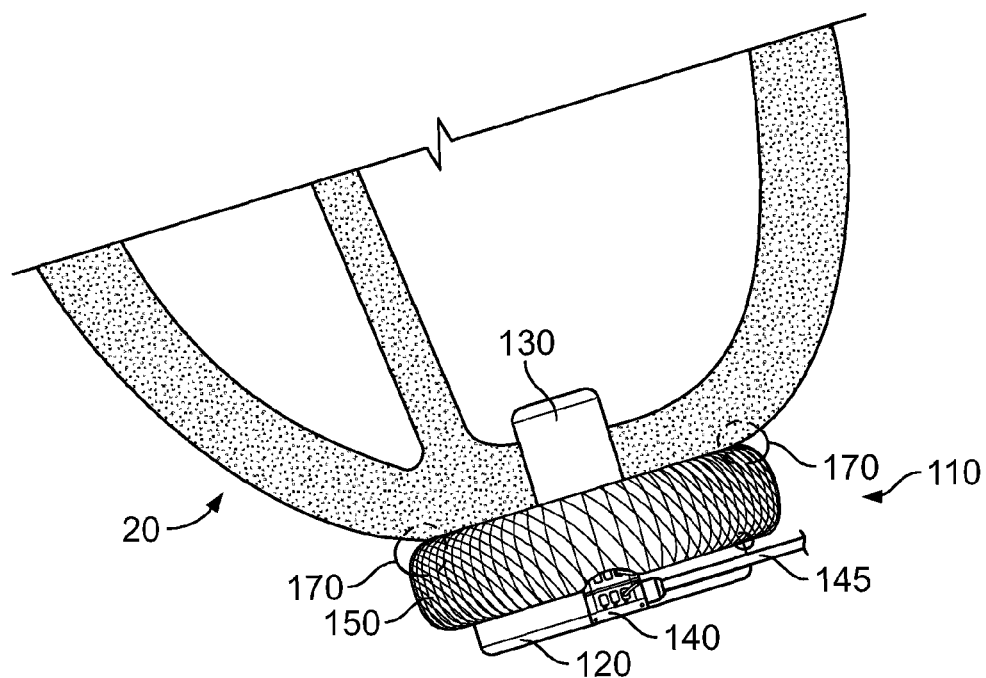
FIGS. 1A-1B are front and rear views, respectively, of an implanted centrifugal blood pump secured to a heart using a mounting cuff.
Figure 1B:
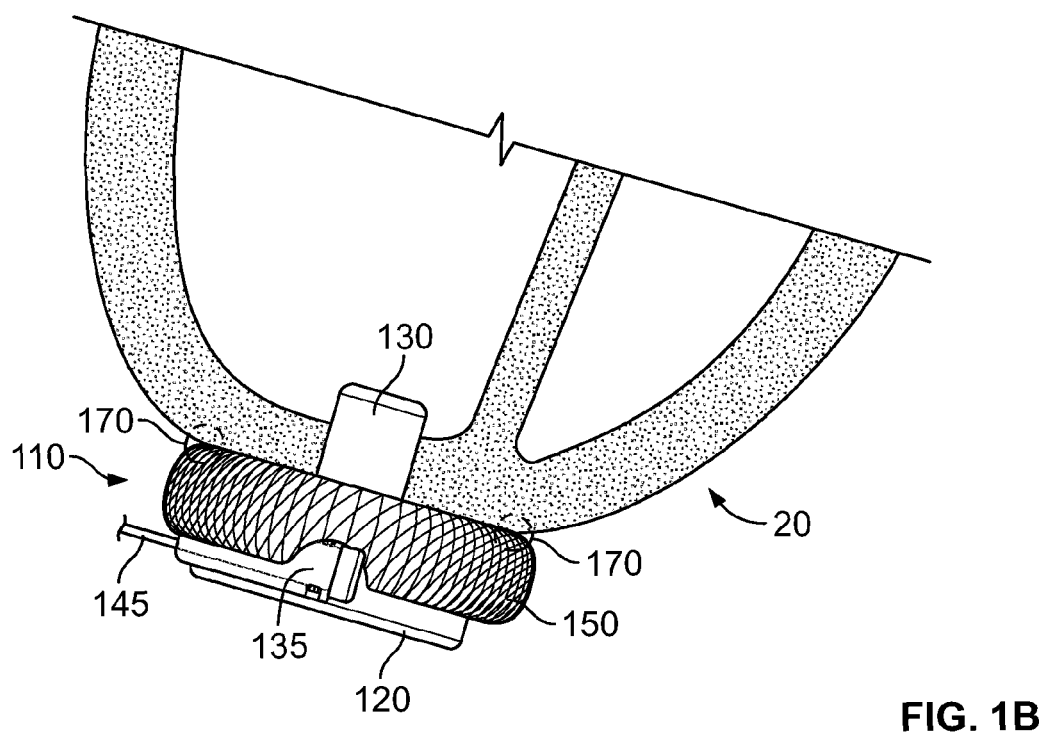

FIGS. 1A-1B are front and rear views, respectively, of a blood pump 110 (e.g., an implanted centrifugal blood pump) secured to a heart 20 using a flexible mounting cuff 150. When implanted in a patient and secured to a heart 20 as depicted in FIGS. 1A-1B, the blood pump 110 is not stationary relative to the chest cavity, but rather moves peri-surgically upon manipulation by the surgeon, especially during chest closure, and post-surgically with the contractions and expansions of the heart 20 and with bulk motion and postural changes of the patient. As such, movements of the heart 20 cause forces on the blood pump 110 (e.g., from the heart itself, tissue surrounding the heart, and the like) that can stress the points of attachment between the blood pump 110 and the heart and can change the relative positions of the pump and heart, e.g. undesirably redirecting the pump's inlet port towards (perpendicular to) the interventricular septum instead of along (parallel to) it. The mounting cuff 150 advantageously has an inside diameter that is at least as large as the outside diameter of the blood pump 110 so as to include a large surface area that can be attached to the heart and to provide maximal mechanical advantage to minimize stress on the attachment points. Additionally, attachment around the outside diameter of the heart pump allows for the pump to be placed adjacent the epicardium without the presence of a gap between the epicardium and a parallel surface of the blood pump housing. Similar attachment to the inlet port provides less mechanical advantage in proportion to the relative diameters of the inlet port and pump's outer surface and requires the presence of a gap between the housing and the epicardium to allow access to that attachment location.

Figure 2:
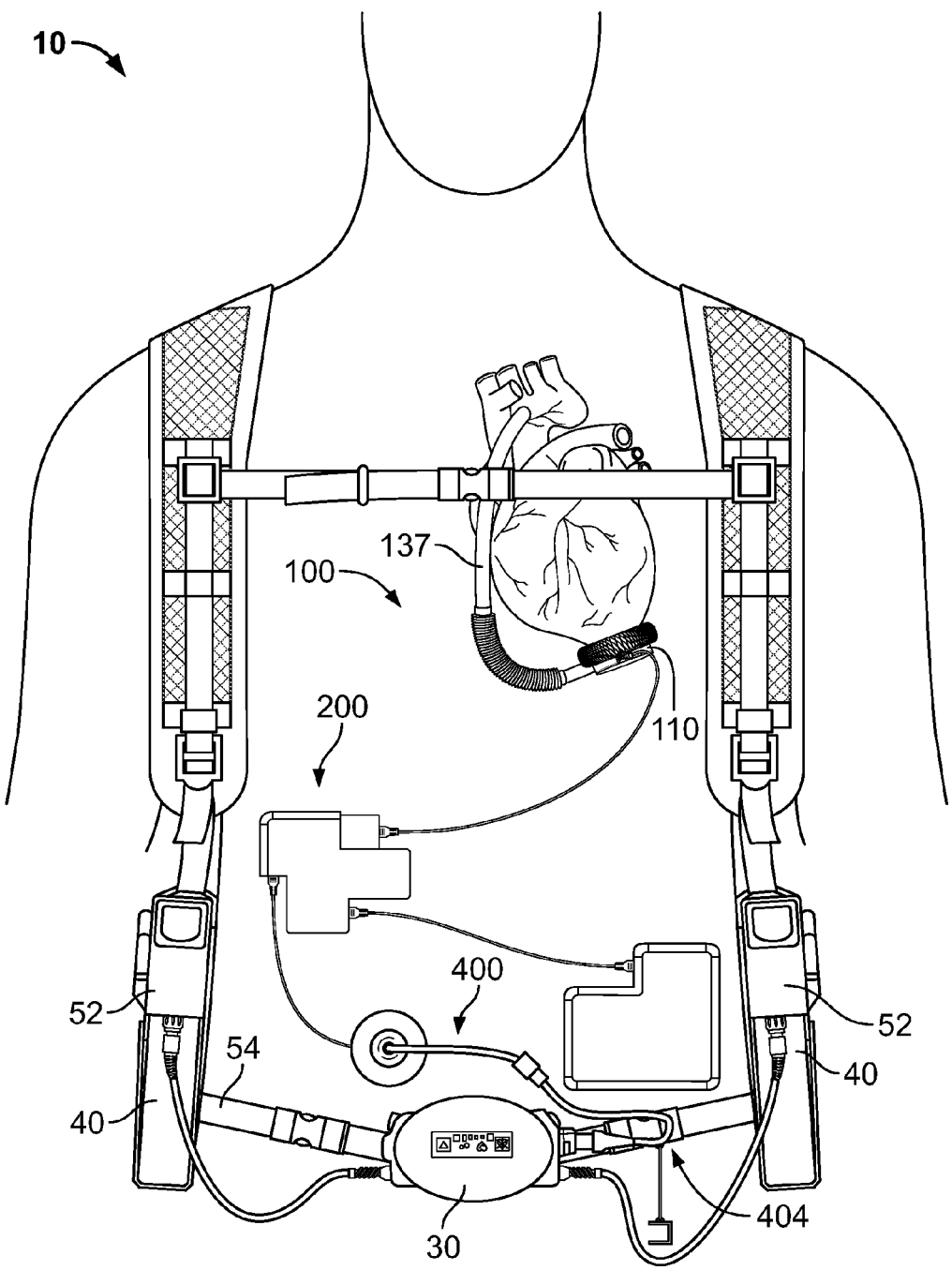
FIG. 2 depicts a front view of a blood pump system, including a pump mounting cuff, implanted in a patient.

The implanted blood pump system, including the mounting cuff, can be part of a larger system. FIG. 2 is a front view depicting an embodiment of a blood pump system 10 coupled to a portable external controller 30 and two external batteries 40. In the embodiment depicted here, the implanted blood pump system 10 includes the internal blood pump assembly 100, a centrifugal blood pump 110, an internal controller assembly 200 (that can internal batteries), and a percutaneous lead 400. The controller assembly 200 can be implanted in, for example, the thorax, the abdomen, or any other part of a patient's body as appropriate and can be electrically connected to the blood pump 110 such that the controller assembly 200 can control functions of and monitor the blood pump 110. Power for normal operation of the system 10 can be supplied by the internal batteries included in the controller assembly 200 or by an external power source (such as the external batteries 40). The blood pump system 10 can be electrically coupled via the percutaneous lead 400 to an external controller and/or power source. The percutaneous lead 400 can include a flexible outer housing enclosing redundant electrical lead sets, for example as discussed in U.S. patent application Ser. No. 12/472,812, filed May 27, 2009, which is hereby incorporated by reference. Other systems including the blood pump and the mounting cuff are also contemplated.

Blood Pump

The blood pump assembly 100 can be a ventricular assist device (VAD). A VAD is a mechanical circulatory device that is used to partially or completely replace the function of a failing heart. Some VADs are intended for short term use, typically for patients recovering from heart attacks or heart surgery, while others are intended for long term use (e.g., months, years, or the remainder of a patient's life), typically for patients suffering from congestive heart failure. VADs are designed to assist either the right (RVAD) or left (LVAD) ventricle, or both at once (BiVAD). Some assist devices are cannulated to the atria instead of the ventricles.

Figure 3:
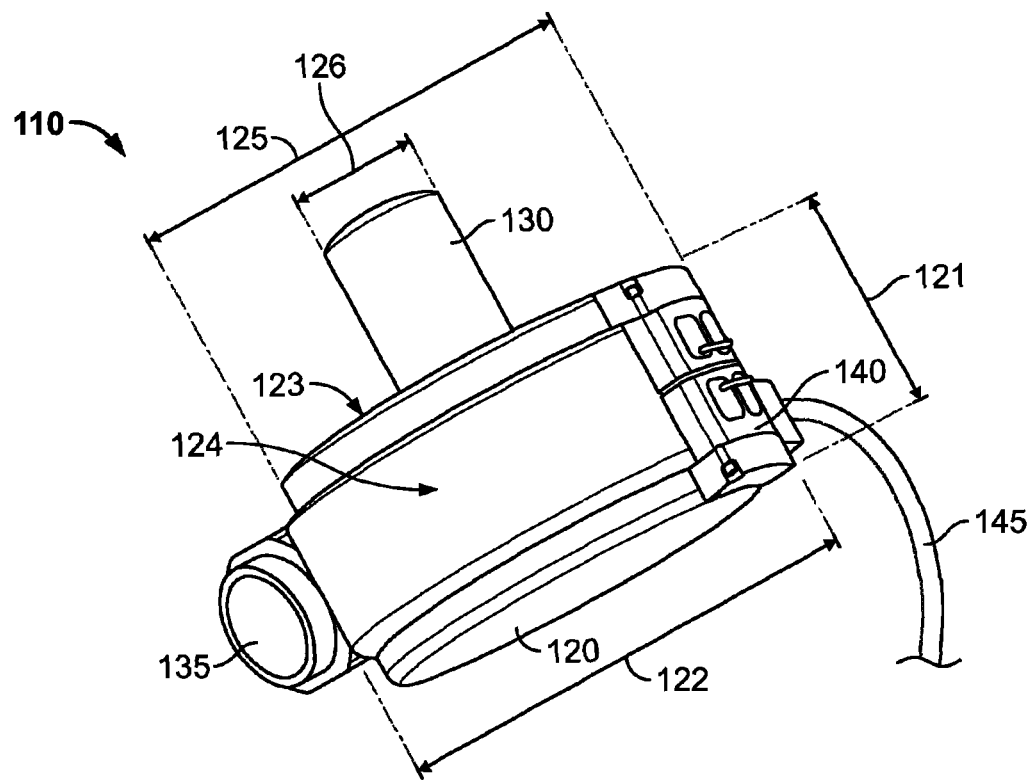
FIG. 3 is a perspective view of a centrifugal blood pump.

Referring to FIGS. 1A, 1B, and 3 (a perspective view of the centrifugal blood pump 110), one embodiment of a centrifugal blood pump 110 can include an outer housing 120 that at least partially contains a motor and hydraulic elements designed to transfer blood from an interior chamber of a heart and return the blood to a circulatory system. The blood pump 110 can have a generally cylindrical shape wherein a height 121 of the housing 120 is smaller than a diameter 122 of the housing 120. The housing 120 can include a generally flat base 123 adapted to be implanted adjacent to the exterior of a heart and has a generally cylindrical perimeter 124 adjacent to the base 123. The base 123 can include an inlet port cannula 130 that traverses the wall of a heart (e.g., at the apex of the heart) and fluidly connects to an interior chamber of the heart with the interior of the blood pump housing 120 so that blood can be drawn by the blood pump 110 from the interior chamber of the heart. The base 123 can have a generally toroidal shape with an outer diameter 125 adjacent and perpendicular to the substantially cylindrical perimeter 124 and an inner diameter 126 that is at least partially defined by the cylindrical inlet port 130.

The blood pump 110 can also include an outlet port 135, located in the perimeter 124 of the housing 120, for expelling blood that has been drawn by the blood pump 110 from the interior chamber of the heart. The outlet port 135 can be fluidly connected via flexible tubing 137 (See FIG. 2) to the aorta such that blood drawn from the interior chamber of the heart can be expelled under pressure into the circulatory system of the user. As such, the blood pump assembly 100 can augment the pumping of blood performed by the heart. The blood pump 110 can also include a fluid-tight bulkhead fitting 140 that allows an electrical conduit 145 to pass from outside the blood pump 110 into the interior of the pump 110, while maintaining a fluid-tight seal.

The housing 120 can include a motor, a rotor, and control electronics. The motor can induce a rotor to turn via electrical coils strategically commutated to 'push' electromagnets imbedded in the rotor with an electromagnetic field. The rotor can contain hydrodynamic elements, e.g. blades, which functions as an impeller that, when rotating, can increase the pressure of fluid within the blood pump 110. Blood can enter the housing 120 through the inlet port cannula 130 and be accelerated inside the housing 120 by the impeller, causing the accelerated blood to flow radially outward and exit through the outlet port 135 where it continues through the flexible tubing 137 and into the circulatory system. The blood pump 110 is advantageously compact and, due in part to the overall mushroom shape, can be readily secured to a heart. In a centrifugal pump, the blood generally enters through an inlet port into the center of the impeller, is diverted perpendicularly by hydrodynamic elements, e.g. blades, thereby imparting the energy of angular acceleration, is collected at the outer aspect of the impeller in a volute, and exits through a diffusing outlet port. The perpendicular diversion of the flow and the consequent perpendicular orientation between the inlet and outlet ports is generally responsible for the characteristic mushroom shape of a centrifugal pump.

Mounting Cuff

Still referring to FIGS. 1A-1B, in some embodiments, the mounting cuff 150 can substantially encircle and be coupled to the outer perimeter of the housing 120 of the blood pump 110. The mounting cuff 150 can be secured to the heart 20 using, for example, medical sutures 170, staples, and the like. Because the mounting cuff 150 substantially encircles the outer perimeter of the housing 120, implantation of the blood pump 110 is simplified and the quality of the attachment to the heart 20 is improved.

Figure 4:
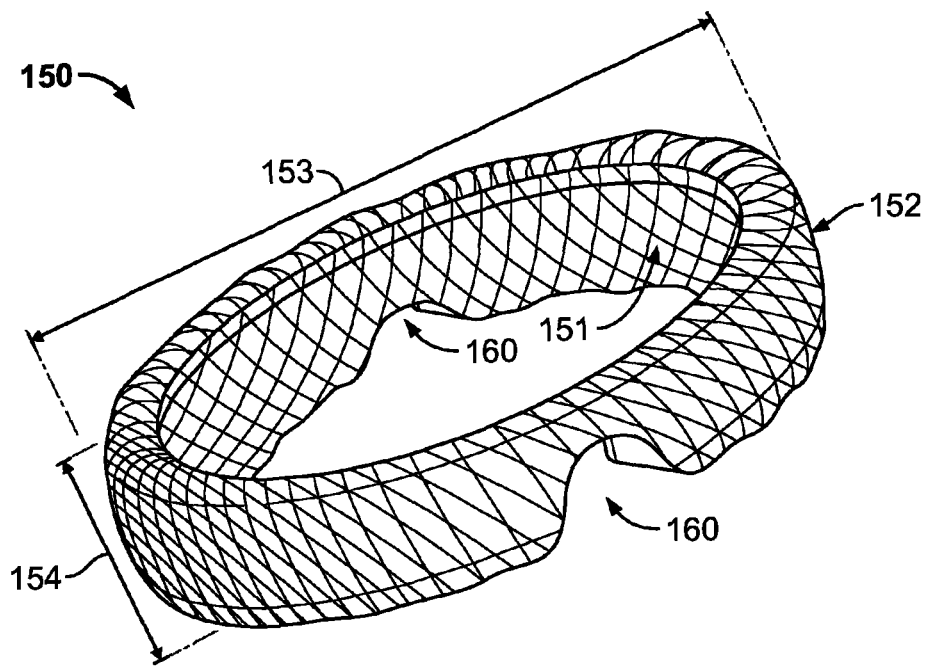
FIG. 4 is a perspective view of a blood pump mounting cuff.

FIG. 4 is a perspective view of a blood pump mounting cuff 150. The cuff 150 can be an individual component, or can be manufactured as part of the blood pump 110. The cuff 150 can comprise flexible materials suitable for implantation such as polyethylene terephthalate (PET) and expanded polytetrafluoroethylene (ePTFE), and include components made of relatively inflexible materials suitable for implantation such as polytetrafluoroethylene (PTFE), polypropylene (PP), polyetheretherketones (PEEK), ultra-high molecular weight polyethylenes (UHMWPE), titanium, nitinol, stainless steel, and combinations of these materials. The mounting cuff 150 can include one or more cut-out regions 160 such that when the mounting cuff 150 is coupled to the blood pump 110, the mounting cuff 150 does not interfere with the outlet port 135 or the bulkhead fitting 140.

The mounting cuff 150 can be configured to encircle a centrifugal blood pump, for example, to be secured to the external wall of the left ventricle of a heart. The mounting cuff 150 can have an inner surface 151 that at least partially matches or conforms to the pump housing 120 when coupled to the pump 110 and an outer surface 152 that is relatively flat or convex in a way that facilitates suturing. The flexible mounting cuff 150 can conform to the outer perimeter of a blood pump housing that is not entirely circular and can conform to blood pumps of varying heights. Flexibility also allows the mounting cuff 150 to conform to an adjacent heart wall that is not entirely flat. During implantation, the mounting cuff can be manipulated to conform to the adjacent heart wall surface before securing in place, for example, with the sutures 170. The mounting cuff 150 described is advantageous if its diameter 153 is greater than the diameter of the inlet port and less than about the diameter of approximately the inferior one-fifth or so of the heart near the apex, i.e. generally between about 0.5 inches and 5 inches (e.g., 0.60 inches, 0.75 inches, 1 inch, 2 inches, 3 inches, and the like); if its height 154 is sufficient to be adequately secured to the pump and provide adequate purchase for suturing to the heart, i.e. generally between about 0.1 inches and 1 inch (e.g., 0.15 inches, 0.24 inches, 1 inch, and the like); and if its thickness is sufficient to be adequately secured to the pump and provide adequate purchase for suturing to the heart, i.e. generally between about 0.05 inches and 0.5 inches thick (e.g. 0.075 inches, 0.1 inches, 0.2 inches, and the like). The mounting cuff 150 may have features on its inner surface 151 to engage mating features on the pump's outer surface 124 for the purpose of securing the mounting cuff to the pump. The mounting cuff 150 may also be of a size and shape that accommodates or is suitable for the use of special surgical tools designed to suture, staple, or assist in the act of suturing, stapling, or other means of mechanically attaching the mounting cuff to the heart.

When the mounting cuff is coupled to the blood pump 110, the blood pump 110 can be coupled to a heart by attaching the cuff 150 to the heart, for example, using sutures, staples, or other known mechanical means. The mounting cuff can be attached to the blood pump and/or the heart either directly or indirectly. In some embodiments, the blood pump 110 can include a soft, flexible region around the perimeter such that cuff 150 can be secured to the blood pump 110 in a manner similar to securing the cuff 150 to a heart. In other embodiments, the mounting cuff 150 can attached to the blood pump 110 by threads, detents, a series of sutures, a series of snaps, a band or strap, a friction fit, and the like. Still, other embodiments may include first attaching a mechanical component onto the heart by staple or suture for acting as a key that fits into a mating portion on the mounting cuff for securing the mounting cuff to the heart. In some embodiments, the mounting cuff is attached to the blood pump during the implantation procedure, before or after attachment of the mounting cuff to an exterior wall of the heart and before or after placement of the blood pump adjacent the exterior wall of the heart. In other embodiments, the mounting cuff 150 can be attached to the blood pump 110 prior to implantation of any of the components into the body.

Figure 5A:
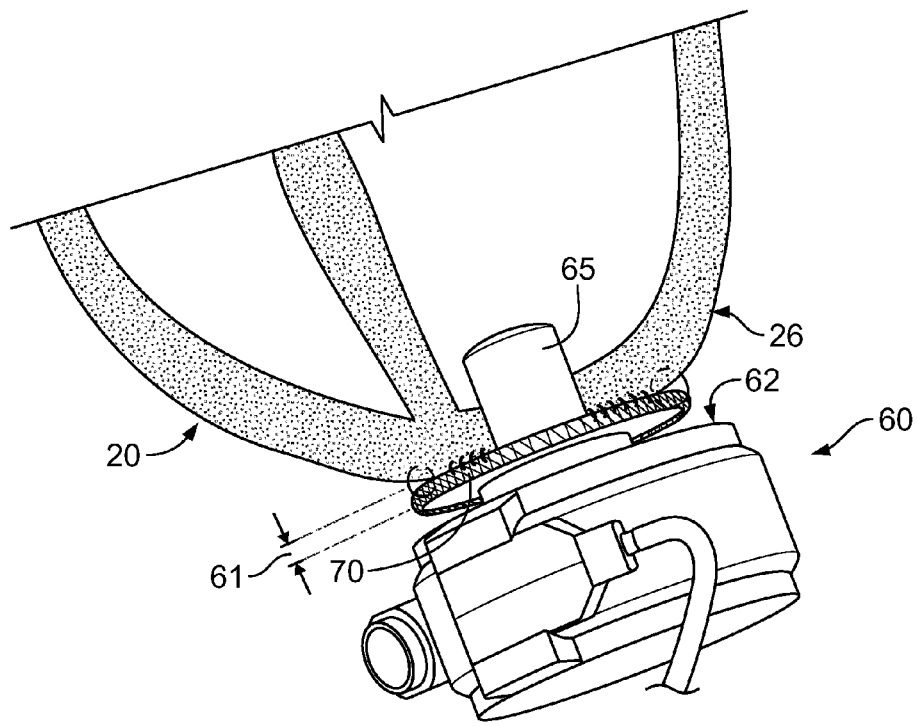
FIG. 5A is a perspective view of an implanted centrifugal blood pump secured to a heart using a flexible mounting cuff positioned around the inlet port.
Figure 5B:
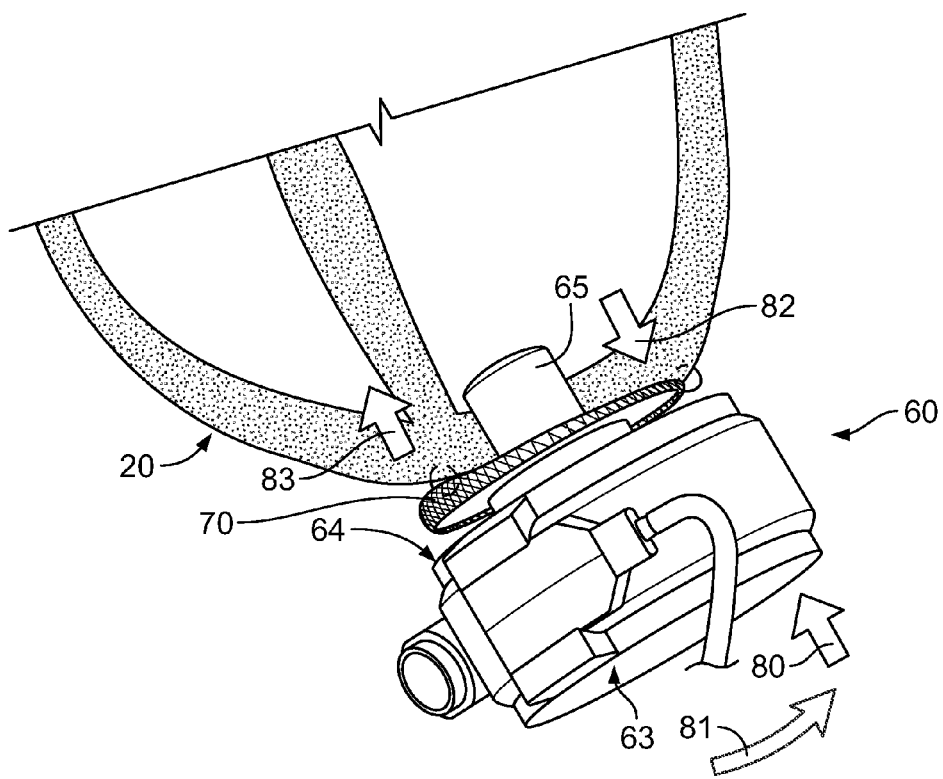
FIG. 5B is a perspective view of the implanted centrifugal blood pump of FIG. 5A, showing an applied force causing the blood pump to pivot with respect to the heart.

In contrast to having a mounting cuff 150 secured to an outer perimeter of a housing 120 of the blood pump, some blood pump attachment systems can encircle smaller portions of the blood pump, such as the inlet port. For example, FIGS. 5A and 5B are perspective views of an implanted centrifugal blood pump 60 secured to a heart 20 using a flexible attachment cuff 70 positioned around the pump inlet cannula 65. FIG. 5B further depicts an applied turning force (i.e. bending moment) causing the blood pump 60 to pivot with respect to the heart 20. This bending moment may be characteristic of peri-surgical manipulation by the surgeon, especially during chest closure, and post-surgical motion due to the contractions and expansions of the heart 20 and bulk motion and postural changes of the patient. As depicted, the blood pump 60 includes the attachment cuff 70 that encircles a pump inlet cannula 65. In order to provide a surgeon access to the attachment cuff 70 for attaching the attachment cuff 70 to the heart wall, the implanted blood pump 60 of FIGS. 5A and 5B is implanted such that a gap 61 exists between the rear face 62 of the blood pump 60 and the exterior surface 26 of the heart 20, which increases the effective size of the pump.

Referring to FIG. 5B, when the blood pump 60 is attached as in FIG. 5A and a bending moment is applied to a portion 63 of the blood pump 60 near the outer perimeter (as indicated by arrow 80), the blood pump 60 can pivot relative to the heart 20 (as indicated by arrow 81). In this example, the portion 63 of the pump 60 near the applied force 80 is pushed toward the wall of the heart, while the portion 64 of the pump 60 opposite the applied force 80 is pivoted away from the wall of the heart. As such, the wall of the heart presses back against the cuff 70, as represented by arrow 82, and pulls back on the cuff 70, as represented by arrow 83. In this example, the forces 81 and 82 that counteract the bending moment are increased in proportion to the outer diameter of the pump and the diameter of the inlet port cannula in accordance with Newton's Law. These higher forces thus cause higher stress on the attachment between the cuff 70 and the heart and/or the inlet port cannula 65. Furthermore, they can result in localized stress at individual attachment points that can result in a detachment, damage to the attachment cuff 70, and/or damage to the heart wall.

Figure 6:
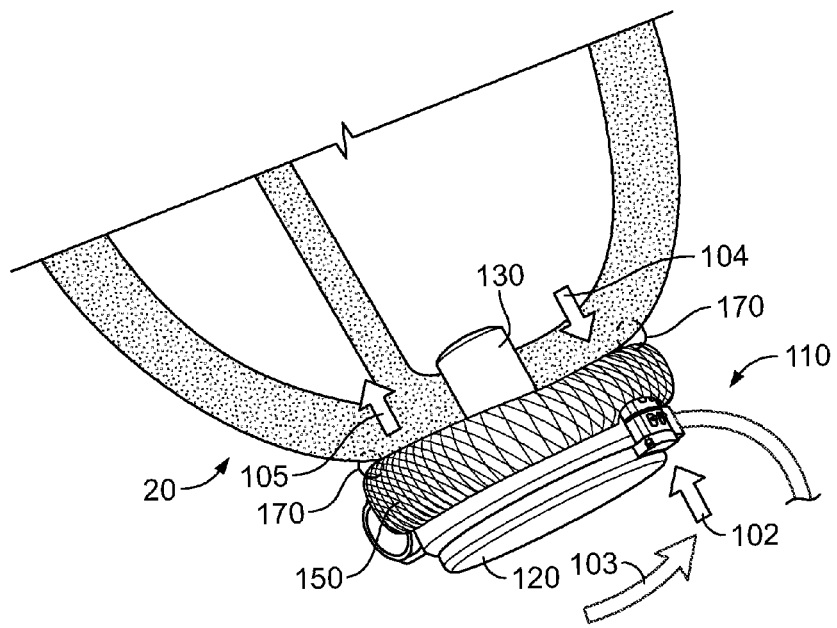
FIG. 6 is a perspective view of the blood pump of FIG. 1A, showing a force applied to the pump housing.

FIG. 6 is a perspective view of the blood pump 110 of FIG. 1A, showing a force applied to the pump housing 120. The blood pump 110, including the mounting cuff 150 that encircles the outer perimeter of the housing 120, can be implanted without a gap or a relatively small gap (e.g., less than 0.05 inches), in contrast to the relatively large gap 61 depicted in FIG. 5A (e.g. about 0.2 inches). This zero gap arrangement reduces the effective size of the pump when implanted. When the blood pump 110 is attached as in FIG. 6 and a bending moment 103 is applied to a portion of the blood pump 110 near the outer perimeter, the counteracting forces indicated by arrows 104 and 105 are smaller than the corresponding forces 82 and 83 shown in FIG. 5B and the stresses are thus reduced. Furthermore, when the mounting cuff 150 encircles the outer perimeter of the housing 120, the region available for attachment can be larger than when a mounting cuff encircles the inlet port 130. This larger region can translate to more attachment points (e.g., more sutures, staples, and the like), greater distance between attachment points, and the like. This can further reduce the stress at an individual attachment point, thus reducing the risk of damage to the mounting cuff 150 and the heart wall. Furthermore, the surgeon has more room to work while suturing the mounting cuff to the heart, potentially simplifying the implant procedure.

In addition to considerations of attachment point stress, the degree of motion is also advantageously reduced with the mounting cuff in FIG. 6 relative to that in FIG. 5A and FIG. 5B. Because the forces that counteract a bending moment are smaller, the angular deviation is proportionally smaller. Most notably, since the position of the inlet port is of primary importance to proper pump function—it ideally is directed parallel to the interventricular septum to avoid causing trauma to any structure within the ventricle, including the endocardium—reducing the angular deviation of the inlet port 130 port is highly desirable.

Implantation Procedure

The blood pump 110 can be implanted in the wall of the left ventricle, e.g. near the apex of the heart. In other embodiments, the blood pump 110 is implanted in the wall of the right ventricle. In other embodiments, the blood pump is attached to an atrium, e.g. if a left ventricle has been resected. The blood pump 110 and the mounting cuff 150 can be secured together prior to implantation into the patient or, in some embodiments, can be secured together after the mounting cuff 150 has been secured to the heart wall. In some embodiments, the blood pump 110 is positioned prior to implanting the mounting cuff 150. In other embodiments, the mounting cuff 150 is positioned prior to implantation of the blood pump 110. After both the mounting cuff 150 and the blood pump 110 are in place, the mounting cuff and the blood pump 110 can be secured together, for example via sutures. For example, the mounting cuff 150 can be coupled loosely to the wall of a heart using the sutures 170. The placement of the mounting cuff can be chosen such that the inlet port 130 of the heart pump 110 will be held adjacent to the left ventricle apex. A scalpel and/or a coring knife can be used to incise a cylindrical opening through the apex into the left ventricle approximately the diameter of the inlet port cannula 130. When the opening has been incised, the inlet port cannula 130 can be advanced into the opening until the pump housing 120 contacts the heart wall. The blood pump 110 can then be secured in place using additional sutures 170 that pass through an outer perimeter section of the blood pump housing and the mounting cuff 150. In some embodiments, the blood pump 110 can include a soft, flexible region around the perimeter such that mounting cuff 150 can be secured to the blood pump 110 in a manner similar to securing the cuff 150 to a heart. In other embodiments, the mounting cuff 150 can attached to the blood pump 110 by threads, detents, a series of sutures, a series of snaps, a band or strap, a friction fit, and the like.

Removable Inlet Cannula

Figure 7:
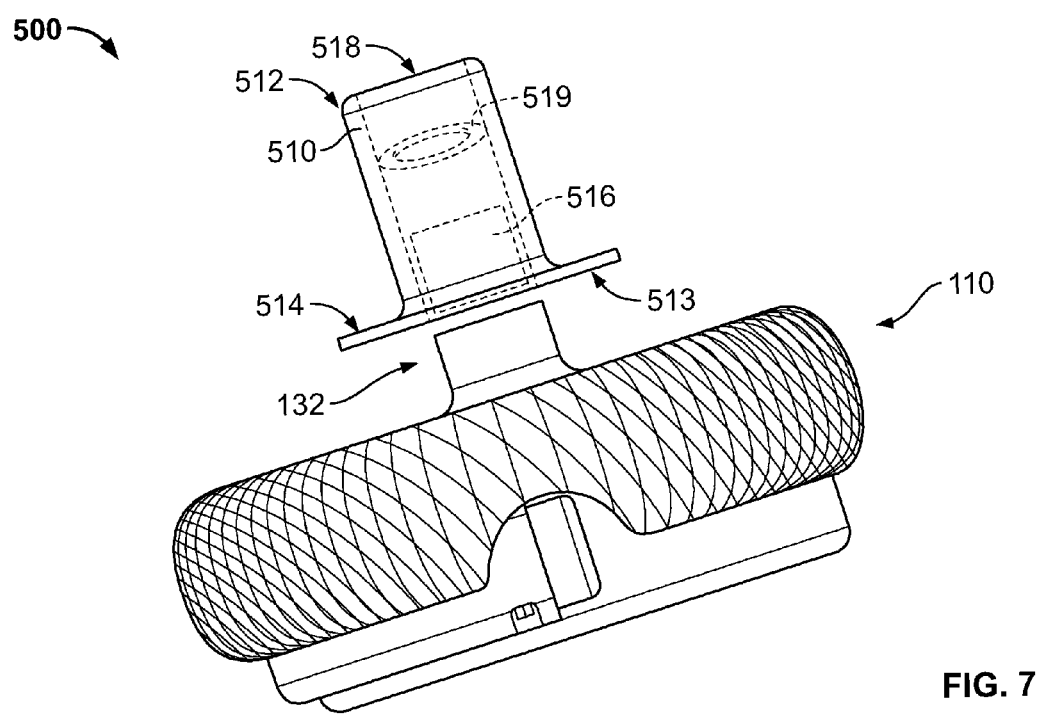
FIG. 7 is a perspective view of a centrifugal blood pump including a removable inlet cannula.

FIG. 7 is a perspective view of a centrifugal blood pump including a removable inlet cannula. A blood pump assembly 500 can include a removable inlet cannula 510 such that the substantially hollow inlet cannula 510 can be implanted in a patient prior to implantation of the blood pump 110. For example, the distal end 512 of the inlet cannula 510 can be inserted into a surgically created opening in the left ventricle of a heart. The inlet cannula 510 can be inserted until the base 514 of the inlet cannula 510 contacts the wall of the heart. When positioned in the opening in the left ventricle, the inlet cannula 510 at least partially defines a fluid pathway between the left ventricle of the heart and the exterior of the heart. In this way, the inlet cannula 510 can be inserted into the opening in the heart prior to placement of the blood pump 110.

In some embodiments, the inlet cannula 510 can include an optional plug 516 located in a fluid channel 518 of the inlet cannula 510 and effectively creating a fluid-tight seal between the plug 516 and the inlet cannula 510. As such, fluid cannot readily pass through the fluid channel 518 between the distal end 512 and a proximal end 513 of the inlet cannula 510. When the inlet cannula 510 that is equipped with the plug 516 is inserted into an opening in the wall of the heart, the inlet cannula 510 can effectively plug the opening, thus limiting the flow of blood from an interior chamber of the heart to the exterior of the heart through the channel 518. In this way, the inlet cannula 510 can be positioned in an opening of the heart and the opening can remain sealed to blood flow for a period of time prior to implantation of the blood pump 110, e.g. potentially obviating cardiopulmonary bypass during the operative procedure. Before implanting the blood pump 110, the plug 516 can be removed from the inlet cannula 510, thus re-establishing a fluid pathway between the interior and the exterior of the heart through the opening in the heart wall. The inlet cannula 510 can optionally include a sewing cuff (not shown) such that the inlet cannula 510 can be held in place by securing the sewing cuff of the cannula 510 to the heart wall, for example, using sutures, staples, and the like. This can be done prior to removal of the plug 516 (if so equipped) so as to maintain the inlet cannula 510 in place prior to implantation of the blood pump 110.

With the inlet cannula 510 placed in an opening in the heart as described above, the plug 516 (if so equipped) can be removed from the inlet cannula 510 and the blood pump 110 can be implanted. For example, the plug 516 can be held in place by threads, detents, friction fit, and the like. Following removal of the plug 516 (if so equipped) the distal end 132 of the inlet port 130 can be inserted into the fluid channel 518 beginning at the proximal end 513 and advanced until a portion of the pump housing 120 contacts the base 514 of the inlet cannula 510. If the base 514 is not already in contact with the wall of a heart, the pump 110 can be further advanced until causing the base 514 to contact the wall of the heart. Blood flow between the inner surface of the fluid channel 18 and the outer surface of the inlet port 130 can be controlled with an optional seal 519 located inside and around the inner circumference of the fluid channel 518. In other embodiments, a seal (not shown) can be positioned around the outer circumference of the inlet port 130 to perform a similar function to that of the optional seal 519. Once in a desired location, the pump 110 can be coupled to the heart by securing the mounting cuff 150 to the heart as described previously. In some embodiments, where the cuff 150 is not secured to the pump housing 120 prior to implantation, the cuff 150 can be secured to the pump housing 120 after implantation, either before, simultaneously with, or after securing the cuff 150 to the heart wall. This can be accomplished by securing the cuff 150 to an attachment ring (not shown), included around the perimeter of the pump housing 120. As with the cuff 150, the attachment ring can comprise materials suitable for implantation such as polyethylene terephthalate (PET), polytetrafluoroethylene (PTFE), expanded polytetrafluoroethylene (ePTFE), polypropylene (PP), polyetheretherketones (PEEK), ultra-high molecular weight polyethylenes (UHMWPE), titanium, nitinol, stainless steel, and combinations of these materials.

In some circumstances, it may be desirable to remove an implanted blood pump. For example, a blood pump may be replaced due to age, damage, replacement with a new model, and the like. In some embodiments, removal of the blood pump 110 can be simplified when using the blood pump 110 and the separate inlet cannula 510. For example, the blood pump 110 can be separated from the heart wall by cutting the sutures, and the like, that secure the cuff 150 to the heart wall. In some circumstances, tissue may have grown in and around the cuff 150 and may be excised. When the cuff 150 has been separated from the heart wall, the blood pump 110 can be simply removed as the inlet port 130 is not in contact with the opening in the heart wall. Once the blood pump 110 is removed, a new blood pump can be implanted by inserting the distal end of the new inlet port 130 into the fluid channel 518 as described above. In this way, removal and replacement of an implanted blood pump is simplified. As an alternative to replacing the blood pump, e.g. in the circumstance in which a patient has recovered native heart function and no longer requires mechanical support, the fluid channel 518 can be sealed using a new plug 516 once the blood pump 110 is removed. In this way, a blood pump 110 can be removed without surgically modifying the opening in the heart into which the blood pump 110 was implanted.

Alternate Embodiments

Figure 8:
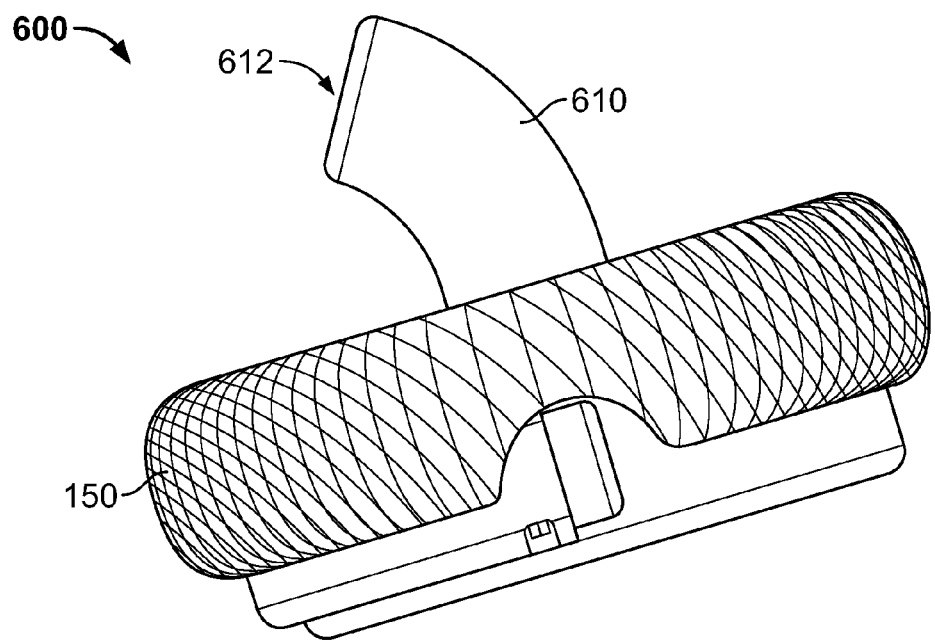
FIG. 8 is a perspective view of a centrifugal blood pump including a curved inlet.

FIG. 8 is a perspective view of a centrifugal blood pump including a curved inlet cannula. A blood pump 600, similar to the blood pump 110, can include a curved inlet port 610. For example, when a blood pump is implanted in the left ventricle of a heart, the blood pump is not stationary relative to the chest cavity, but rather moves with the contractions and expansions of the heart. As such, movements of the heart cause forces on the blood pump 600 (e.g., from the heart itself, tissue surrounding the heart, and the like) that can cause the blood pump 600 to pivot relative to the heart. In some circumstances, pivoting of the blood pump 600 can cause the inlet cannula 610 to tilt such that the opening of the inlet cannula 610 tilts toward an internal structure of the heart, such as the septum (separating the left and right ventricles), as depicted in FIG. 5B. In some cases, the pump can pivot such that septum can interfere with blood flow from the interior chamber of the heart into the inlet cannula 610. As such, the curved inlet cannula 610 can be advantageously configured and implanted such that a distal opening 612 of the inlet cannula 610 points away from internal structures of the heart, regardless of the contractile state of the heart.

Figure 9:
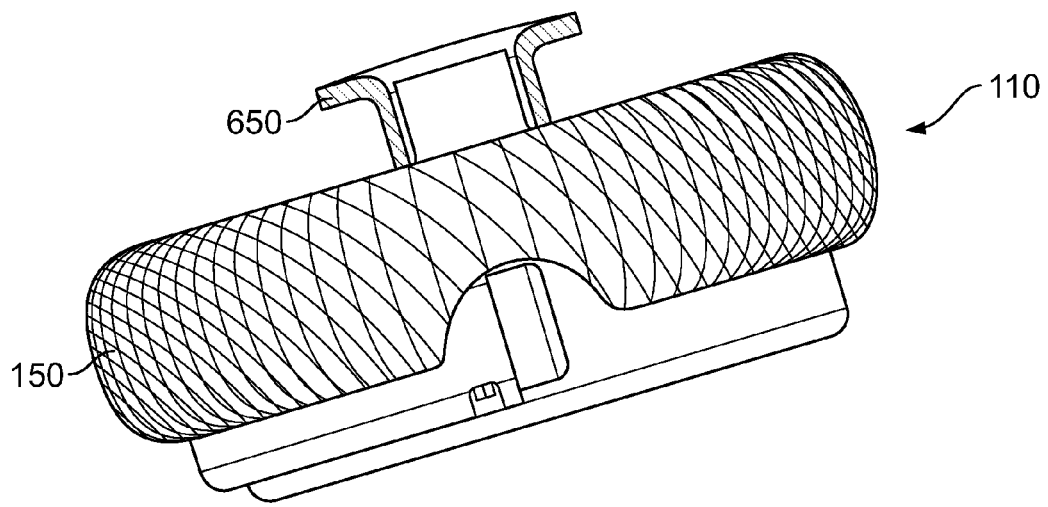
FIG. 9 is a perspective view of a centrifugal blood pump including a hemostatic cannula.

FIG. 9 is a perspective view of a centrifugal blood pump including an inlet cannula 650 shaped to provide improved patency of the fluid channel between the ventricle and the heart. Intet cannula 650 has a flanged distal end. A distal end larger than the opening can make the inlet port more difficult to pull out while creating a better seal against the interior wall of the heart chamber. Prior to implantation of the blood pump 110, the inlet cannula 650 or otherwise advantageously shaped inlet cannula can be inserted in a surgically prepared opening the wall of the heart. The inlet cannula 650 can be removably attached to the remainder of the heart pump 110.

A number of embodiments have been described. Nevertheless, it will be understood that various modifications may be made without departing from the spirit and scope of this disclosure. Accordingly, other embodiments are within the scope of the following claims.

What is claimed is:

1. A method of implanting a blood pump system in a patient requiring treatment, comprising:
   creating an opening in an epicardium of a heart to access an interior chamber of the heart;
   implanting a blood pump such that an inlet port of a pump housing is in fluid communication with the interior chamber of the heart through the opening and a first external surface adjacent to the inlet port is substantially adjacent to the epicardium of the heart, the blood pump being adapted to transfer blood from the inlet port to an outlet port;
   fluidly connecting the outlet port to the circulatory system; and
   securing a mounting cuff to the exterior wall of the heart, the mounting cuff is adapted to couple to a second external surface of the pump housing, the second external surface is located adjacent to the first external surface and at least partially defining an outside perimeter of the pump housing.

2. The method of claim 1, further comprising:
   implanting an inlet cannula, the inlet cannula adapted to traverse the wall of the heart, and the inlet cannula including an interior channel that fluidly connects the interior chamber of the heart with the inlet port of the pump housing; and coupling the pump housing to the inlet cannula.

3. The method of claim 1, wherein the mounting cuff is secured to the exterior wall of the heart while the first surface of the pump housing is positioned substantially adjacent to the epicardium of the heart.

4. The method of claim 1, wherein implanting the pump housing comprises advancing the inlet port through the opening until the pump housing contacts the epicardium of the heart.

5. The method of claim 1, further comprising securing the mounting cuff to the second external surface of the pump housing.

6. The method of claim 5, wherein the step of securing the mounting cuff to the second external surface of the pump housing is preformed prior to the step of securing the mounting cuff to the epicardium of the heart.

7. The method of claim 5, wherein the step of securing the mounting cuff to the epicardium of the heart is preformed prior to the step of securing the mounting cuff to the second external surface of the pump housing.

8. The method of claim 5, wherein securing the mounting cuff to the second external surface of the pump housing comprises securing the mounting cuff to the second external surface of the pump housing with sutures or staples.

9. The method of claim 1, wherein the second external surface of the pump housing is substantially cylindrical and is substantially perpendicular to the first external surface, the first external surface being substantially toroidal.

10. The method of claim 1, further comprising, prior to the implanting, removably attaching an inlet cannula defining the inlet port to the pump housing.

11. The method of claim 10, wherein the inlet port is blocked by a removable plug fit within the inlet port when the blood pump is implanted.

12. The method of claim 11, further comprising removing the removable plug from the inlet port.

13. The method of claim 1, wherein securing the mounting cuff to the exterior wall of the heart comprises securing the mounting cuff to the exterior wall of the heart with sutures.

14. The method of claim 1, wherein securing the mounting cuff to the exterior wall of the heart comprises securing the mounting cuff to the exterior wall of the heart with staples.

15. The method of claim 1, wherein the implanting comprises manipulating the mounting cuff to conform to the exterior wall of the heart.

16. A method of implanting a blood pump system in a patient requiring treatment, comprising:

creating an opening in an epicardium of a heart to access an interior chamber of the heart;

implanting a blood pump that includes a pump housing having a first external surface and an inlet port that extends from the first external surface prior to implantation of the blood pump such that the inlet port of the pump housing is inserted in the opening and the first external surface of the pump housing contacts the epicardium of the heart surrounding the opening; and securing the blood pump to the heart with a mounting cuff while the first external surface of the pump housing is in contact with the epicardium of the heart surrounding the opening.

17. The method of claim 16, wherein the mounting cuff is secured to a second external surface of the pump housing, the second external surface being located adjacent to the first external surface and at least partially defining an outside perimeter of the pump housing.

18. The method of claim 17, wherein the second external surface of the pump housing is substantially cylindrical and is substantially perpendicular to the first external surface, the first external surface being substantially toroidal.

19. The method of claim 17, wherein the inlet port is blocked by a removable plug fit within the inlet port when the blood pump is implanted.

20. The method of claim 19, further comprising removing the removable plug from the inlet port.

21. The method of claim 17, wherein securing the blood pump to the heart with a mounting cuff comprises securing the mounting cuff to the epicardium with sutures or staples.

22. The method of claim 17, wherein securing the blood pump to the heart with a mounting cuff comprises securing the mounting cuff to the blood pump with sutures or staples.

23. The method of claim 17, further comprising manipulating the mounting cuff to conform to the exterior wall of the heart.

24. A method of implanting a blood pump system in a patient requiring treatment, comprising:

creating an opening in an epicardium of a heart to access an interior chamber of the heart;

implanting a blood pump such that an inlet port of a pump housing is inserted in the opening and a first external surface adjacent to the inlet port contacts the epicardium of the heart surrounding the opening; and securing the blood pump to the heart with a mounting cuff while the first external surface of the pump housing is in contact with the epicardium of the heart surrounding the opening, wherein the mounting cuff is secured to a second external surface of the pump housing, the second external surface being located adjacent to the first external surface and at least partially defining an outside perimeter of the pump housing.

* * * * *